(12) United States Patent
Brownlee

(10) Patent No.: US 6,282,303 B1
(45) Date of Patent: Aug. 28, 2001

(54) METHOD AND APPARATUS FOR SCANNING A FINGERPRINT USING A LINEAR SENSOR WITHIN A CURSOR CONTROL DEVICE

(75) Inventor: Kenneth Brownlee, Palo Alto, CA (US)

(73) Assignee: Digital Persona, Inc., Redwood City, CA (US)

( * ) Notice: Subject to any disclaimer, the term of this patent is extended or adjusted under 35 U.S.C. 154(b) by 0 days.

(21) Appl. No.: 09/591,029

(22) Filed: Jun. 9, 2000

Related U.S. Application Data

(63) Continuation-in-part of application No. 09/089,316, filed on Jun. 2, 1998.

(51) Int. Cl.$^7$ .............................. G06K 9/00; G06K 9/20; G06G 5/08
(52) U.S. Cl. ........................... 382/124; 382/323; 345/163
(58) Field of Search .................................. 382/124, 127, 382/125, 126, 115, 323, 312, 315; 356/71; 345/163

(56) References Cited

U.S. PATENT DOCUMENTS

| | | | |
|---|---|---|---|
| 3,419,287 | 12/1968 | Rudie et al. | 283/69 |
| 3,423,886 | 1/1969 | Schpak et al. | 451/43 |
| 3,482,498 | 12/1969 | Becker | 396/15 |
| 3,872,438 | 3/1975 | Cuttill et al. | 235/381 |
| 3,959,884 | 6/1976 | Jordan et al. | 283/169 |
| 3,975,711 | 8/1976 | McMahon | 382/126 |
| 4,032,889 | 6/1977 | Nassimbene | 382/115 |
| 4,047,154 | 9/1977 | Vitols et al. | 382/125 |
| 4,151,512 | 4/1979 | Riganati et al. | 382/125 |
| 4,156,230 | 5/1979 | Riganati et al. | 382/124 |
| 4,185,270 | 1/1980 | Fischer, II et al. | 382/125 |
| 4,208,651 | 6/1980 | McMahon | 382/125 |
| 4,210,899 | 7/1980 | Swonger et al. | 382/125 |
| 4,225,850 | 9/1980 | Chang et al. | 382/124 |
| 4,253,086 | 2/1981 | Szwarcbier | 382/126 |
| 4,260,979 | 4/1981 | Smith | 382/313 |
| 4,322,163 | 3/1982 | Schiller | 356/71 |
| 4,414,684 | 11/1983 | Blonder | 382/127 |
| 4,449,189 | 5/1984 | Feix et al. | 704/272 |
| 4,454,610 | 6/1984 | Sziklai | 382/119 |
| 4,455,083 | 6/1984 | Elmes | 356/71 |
| 4,525,859 | 7/1985 | Bowles et al. | 382/125 |
| 4,544,267 | 10/1985 | Schiller | 356/71 |

(List continued on next page.)

FOREIGN PATENT DOCUMENTS

| | | | |
|---|---|---|---|
| 4125198 | 5/1992 | (DE) | G06K/19/073 |
| 0159037 | 10/1985 | (EP) | G07C/9/00 |
| 0905646A1 * | 3/1999 | (EP) | G06K/11/18 |
| 1283748 | 8/1972 | (GB) | G06F/15/30 |
| 3-292578 | 12/1991 | (JP) | G06K/9/00 |
| 4-158434 * | 6/1992 | (JP) | G06F/3/033 |
| 5-89324 | 4/1993 | (JP) | G07D/9/00 |
| 10079071 * | 9/1996 | (JP) | G06T/1/00 |
| 8203286 | 9/1982 | (WO) | G07C/11/00 |
| 9107728 | 5/1991 | (WO) | G06K/9/00 |

OTHER PUBLICATIONS

Igaki, et al., "Real–Time Fingerprint Sensor Using A Hologram," Applied Optics, vol.31, No. 11 Apr. 10, 1992, pp. 1794–1802.

(List continued on next page.)

*Primary Examiner*—Wenpeng Chen
(74) *Attorney, Agent, or Firm*—Blakely, Sokoloff, Taylor & Zafman LLP

(57) ABSTRACT

A method and apparatus for scanning a fingerprint using a linear optical sensor. A finger or palm is rolled over a transparent roller. A light source directs light through the roller to illuminate or detect the finger. Light directed through the roller is focused onto a linear imaging device. A full 2D recreation of the fingerprint is assembled from the discrete line-image data collected by the linear array imaging sensor. The apparatus contains a rotation detector to detect rotational movement of the roller.

20 Claims, 12 Drawing Sheets

U.S. PATENT DOCUMENTS

| | | | |
|---|---|---|---|
| 4,553,837 | 11/1985 | Marcus | 356/71 |
| 4,581,760 | 4/1986 | Schiller et al. | 382/124 |
| 4,607,384 | 8/1986 | Brooks | 382/124 |
| 4,618,988 | 10/1986 | Schiller | 382/125 |
| 4,636,622 | 1/1987 | Clark | 235/380 |
| 4,641,350 | 2/1987 | Bunn | 382/124 |
| 4,646,352 | 2/1987 | Asai et al. | 382/125 |
| 4,685,145 | 8/1987 | Schiller | 382/272 |
| 4,696,046 | 9/1987 | Schiller | 382/125 |
| 4,698,751 | 10/1987 | Parvin | 712/19 |
| 4,723,298 | 2/1988 | Schiller | 382/251 |
| 4,728,186 | 3/1988 | Eguchi et al. | 356/71 |
| 4,747,147 | 5/1988 | Sparrow | 382/125 |
| 4,752,966 | 6/1988 | Schiller | 382/125 |
| 4,777,651 | 10/1988 | McCann et al. | 382/242 |
| 4,784,484 | 11/1988 | Jensen | 356/171 |
| 4,787,742 | 11/1988 | Schiller et al. | 356/71 |
| 4,790,564 | 12/1988 | Larcher et al. | 283/69 |
| 4,805,223 | 2/1989 | Denyer | 382/127 |
| 4,811,414 | 3/1989 | Fishbine et al. | 382/272 |
| 4,817,183 | 3/1989 | Sparrow | 382/125 |
| 4,827,527 | 5/1989 | Morita et al. | 382/127 |
| 4,837,843 | 6/1989 | Owechko | 382/211 |
| 4,876,725 | 10/1989 | Tomko | 382/126 |
| 4,876,726 | 10/1989 | Capello et al. | 382/124 |
| 4,891,503 | 1/1990 | Jewell | 235/380 |
| 4,896,363 | 1/1990 | Taylor et al. | 382/125 |
| 4,906,070 | 3/1990 | Cobb | 359/834 |
| 4,907,156 | 3/1990 | Doi et al. | 382/130 |
| 4,933,976 | 6/1990 | Fishbine et al. | 382/127 |
| 4,944,021 | 7/1990 | Hoshino et al. | 382/125 |
| 4,947,442 | 8/1990 | Tanaka et al. | 382/125 |
| 4,947,443 | 8/1990 | Costello | 382/125 |
| 4,956,870 | 9/1990 | Hara | 382/124 |
| 4,993,068 | 2/1991 | Piosenka et al. | 713/186 |
| 4,995,086 | 2/1991 | Lilley et al. | 382/124 |
| 5,040,223 | 8/1991 | Kamiya et al. | 382/127 |
| 5,040,224 | 8/1991 | Hara | 382/124 |
| 5,050,220 | 9/1991 | Marsh et al. | 382/124 |
| 5,053,608 | 10/1991 | Senanayake | 235/380 |
| 5,054,090 | 10/1991 | Knight et al. | 382/127 |
| 5,056,892 | 10/1991 | Cobb | 235/380 |
| 5,067,162 | 11/1991 | Driscoll, Jr. et al. | 382/126 |
| 5,095,194 | 3/1992 | Barbanell | 235/379 |
| 5,101,436 | 3/1992 | DeAguiar et al. | 382/241 |
| 5,105,467 | 4/1992 | Kim et al. | 382/125 |
| 5,109,428 | 4/1992 | Igaki et al. | 382/125 |
| 5,144,680 | 9/1992 | Kobayashi et al. | 382/124 |
| 5,151,945 | 9/1992 | Lee et al. | 382/103 |
| 5,175,593 | 12/1992 | Kumagai et al. | 356/171 |
| 5,187,747 | 2/1993 | Capello et al. | 528/503 |
| 5,187,748 | 2/1993 | Lee | 382/127 |
| 5,210,797 | 5/1993 | Usui | 382/126 |
| 5,222,152 | 6/1993 | Fishbine et al. | 382/127 |
| 5,222,153 | 6/1993 | Beiswenger | 382/127 |
| 5,230,025 | 7/1993 | Fishbine et al. | 382/127 |
| 5,239,590 | 8/1993 | Yamamoto | 382/125 |
| 5,287,090 | * 2/1994 | Grant | 345/163 |
| 5,402,324 | 3/1995 | Yokoyama et al. | 362/19 |
| 5,412,463 | 5/1995 | Sibbald | 356/171 |
| 5,416,573 | 5/1995 | Sartor | 356/71 |
| 5,448,649 | 9/1995 | Chen et al. | 382/126 |
| 5,448,659 | 9/1995 | Tsutsui et al. | 385/14 |
| 5,456,256 | 10/1995 | Schneider et al. | 600/445 |
| 5,467,403 | 11/1995 | Fishbine | 382/116 |
| 5,493,621 | 2/1996 | Matsumura | 382/125 |
| 5,505,222 | 4/1996 | Lee | 135/24 |
| 5,509,083 | 4/1996 | Abtahi et al. | 382/124 |
| 5,513,272 | 4/1996 | Bogosian | 382/116 |
| 5,522,623 | 6/1996 | Soules et al. | 283/91 |
| 5,524,069 | 6/1996 | Inoue | 382/270 |
| 5,524,161 | 6/1996 | Omori et al. | 382/125 |
| 5,530,757 | 6/1996 | Krawczyk | 713/188 |
| 5,541,994 | 7/1996 | Tomko et al. | 380/30 |
| 5,546,471 | * 8/1996 | Merjanian | 382/124 |
| 5,563,345 | 10/1996 | Kersten et al. | 73/602 |
| 5,572,597 | 11/1996 | Chang et al. | 382/125 |
| 5,596,454 | 1/1997 | Hebert | 359/726 |
| 5,613,012 | 3/1997 | Hoffman et al. | 382/115 |
| 5,619,586 | 4/1997 | Sibbald | 382/127 |
| 5,623,552 | 4/1997 | Lane | 382/124 |
| 5,625,448 | 4/1997 | Ranalli et al. | 356/71 |
| 5,644,645 | 7/1997 | Osuga | 382/124 |
| 5,650,864 | 7/1997 | Tseng et al. | 358/475 |
| 5,668,603 | 9/1997 | Copeland | 348/473 |
| 5,680,205 | 10/1997 | Borza | 356/71 |
| 5,680,460 | 10/1997 | Tomko et al. | 713/186 |
| 5,712,912 | 1/1998 | Tomko et al. | 713/186 |
| 5,732,148 | 3/1998 | Keagy et al. | 382/124 |
| 5,737,420 | 4/1998 | Tomko et al. | 380/285 |
| 5,740,276 | 4/1998 | Tomko et al. | 382/210 |
| 5,793,881 | 8/1998 | Stiver et al. | 382/115 |
| 5,796,858 | 8/1998 | Zhou et al. | 382/127 |
| 5,801,681 | 9/1998 | Sayag | 345/157 |
| 5,818,956 | 10/1998 | Tuli | 382/126 |
| 5,822,445 | 10/1998 | Wong | 382/127 |
| 5,838,306 | * 11/1998 | O'Connor | 381/124 |
| 5,859,420 | 1/1999 | Borza | 250/208.1 |
| 5,920,384 | 7/1999 | Borza | 356/71 |
| 6,021,212 | 2/2000 | Ho | 382/124 |
| 6,148,094 | * 11/2000 | Kinsella | 382/124 |

OTHER PUBLICATIONS

Supplementary European Search Report, PCT/US95/11427, and Int'l Search Report, 19 pages.

International Search Report, PCT/US99/11912, 6 pages.

International Search Report PCT/US97/08084, Sep. 5, 1997, 5 pages.

Int'l Search Report WO97/43735, Nov. 20, 1997 for Int'l Appln No. PCT/US97/08084, 20 pages.

"3M™ Image Directing Film (IDF) II Sending Light off in the right direction," 3M "Electronic Display Lighting, literature sales", 1 page.

"3M™ Transmissive Right Angle Film (TRAF) II, All the right angles to do two jobs," 3M Electronic Lighting, literature sales, 1 page.

"3M ™ Brightness Enhancement Film (BEF) II, A brilliant solution for improved backlight efficiency," 3M Electronic Lighting, literature sales 1page.

"3M™ Brightness Enhancement Film (BEF)II," 3M "Electronic Display Lighting," 4 pages.

* cited by examiner

METHOD AND APPARATUS FOR SCANNING A FINGERPRINT USING A LINEAR SENSOR WITHIN A CURSOR CONTROL DEVICE

RELATED CASE

This patent application is a continuation-in-part of application Ser. No. 09/089,316, filed Jun. 2, 1998, entitled "Method And Apparatus For Scanning A Fingerprint Using A Linear Sensor."

FIELD OF THE INVENTION

This invention relates generally to a fingerprint scanning system, and more particularly to a method and apparatus for scanning a fingerprint using a linear sensor.

BACKGROUND OF THE INVENTION

Automatic fingerprint scanners are commonly used to obtain an analog or digital image for security, access, verification, or record-keeping applications. In most conventional scanners, a two-dimensional (2D) image of the fingerprint is captured by an imaging device having a matrix of picture elements or pixels arranged as multiple rows and columns. A 2D light-sensitive electronic sensor, such as a charge-coupled device (CCD), is typically used to capture a fingerprint image. However, the cost and size of a typical CCD and associated optics may make it expensive or impractical for use in some constrained physical environments, such as keyboards, laptop computers, and pointing devices such as a mouse or trackball.

One known system uses a series of thermal sensors configured in a cross-shaped, L-shaped or T-shaped pattern having a single column and a single row. When a user slides his or her finger along the sensors, the column sensors are used to determine the position and speed of the finger, and the row sensors are used to obtain an image of the fingerprint. However, the thermal system does not prevent against possible distortion of the fingerprint image from either the stretching of the skin on the finger or the flattening of the ridges and valleys of the fingerprint due to excess pressure.

Therefore, there is a need for a small and inexpensive way of scanning a fingerprint in a constrained physical environment that does not distort the fingerprint image.

SUMMARY OF THE INVENTION

The present invention provides a method and apparatus for scanning a fingerprint using a linear optical sensor. A finger or palm is rolled over a roller. A light source directs light through the roller to illuminate or detect the finger. Light directed through the roller is focused onto a linear imaging device. A full 2D recreation of the fingerprint is assembled from the discrete line-image data collected by the linear array imaging sensor. The apparatus contains a rotation detector to detect rotational movement of the roller.

For one embodiment, the transparent roller is part of a human interface device, such as a pointing device or keyboard. For one embodiment, the cursor control device may be a separate cursor control device or a scroll bar for a trackball or mouse. For one embodiment, the system recognizes when the pointing device is over an authentication area. For one embodiment, the roller lights up in that instance, to indicate to the user that the user should slide his or her finger along the roller for authentication. If the user does so, the system automatically inserts the fingerprint, password, or other authenticating information into the area that requested the authentication information.

BRIEF DESCRIPTION OF THE DRAWINGS

The present invention is illustrated by way of example and may be better understood by referring to the following description in conjunction with the accompanying drawings, in which like references indicate similar elements and in which.

DETAILED DESCRIPTION

In the following description of a preferred embodiment, reference is made to the accompanying drawings that form a part hereof, and in which is shown by way of illustration a specific embodiment in which the invention may be practiced. It is to be understood that other embodiments may be utilized and structural changes may be made without departing from the scope of the present invention. A preferred embodiment of the present invention, described below, enables a remote computer system user to execute a software application on a network file server.

In the following description, for purposes of explanation, numerous specific details are set forth in order to provide a thorough understanding of the present invention. It will be evident, however, to one skilled in the art that the present invention may be practiced without these specific details. In other instances, well-known structures and devices are shown in block diagram form in order to facilitate description.

The present invention offers several advantages over existing systems. A linear imaging device and the associated optical components are typically smaller and less expensive than a 2D sensor array and its associated optics, making the present invention smaller and cheaper to manufacture than existing systems. The use of a roller with the present invention reduces distortion of the skin of the finger due to stretching, and provides an improved image quality due to roller pressure on the small line of the finger. As described below, the fingerprint image is generated in series, rather than parallel, reducing the cost of associated electronics. The present invention is also more tolerant of various optics and focal lengths, since the image only must be focused in one dimension, making the present invention easier to manufacture.

Figure 1:
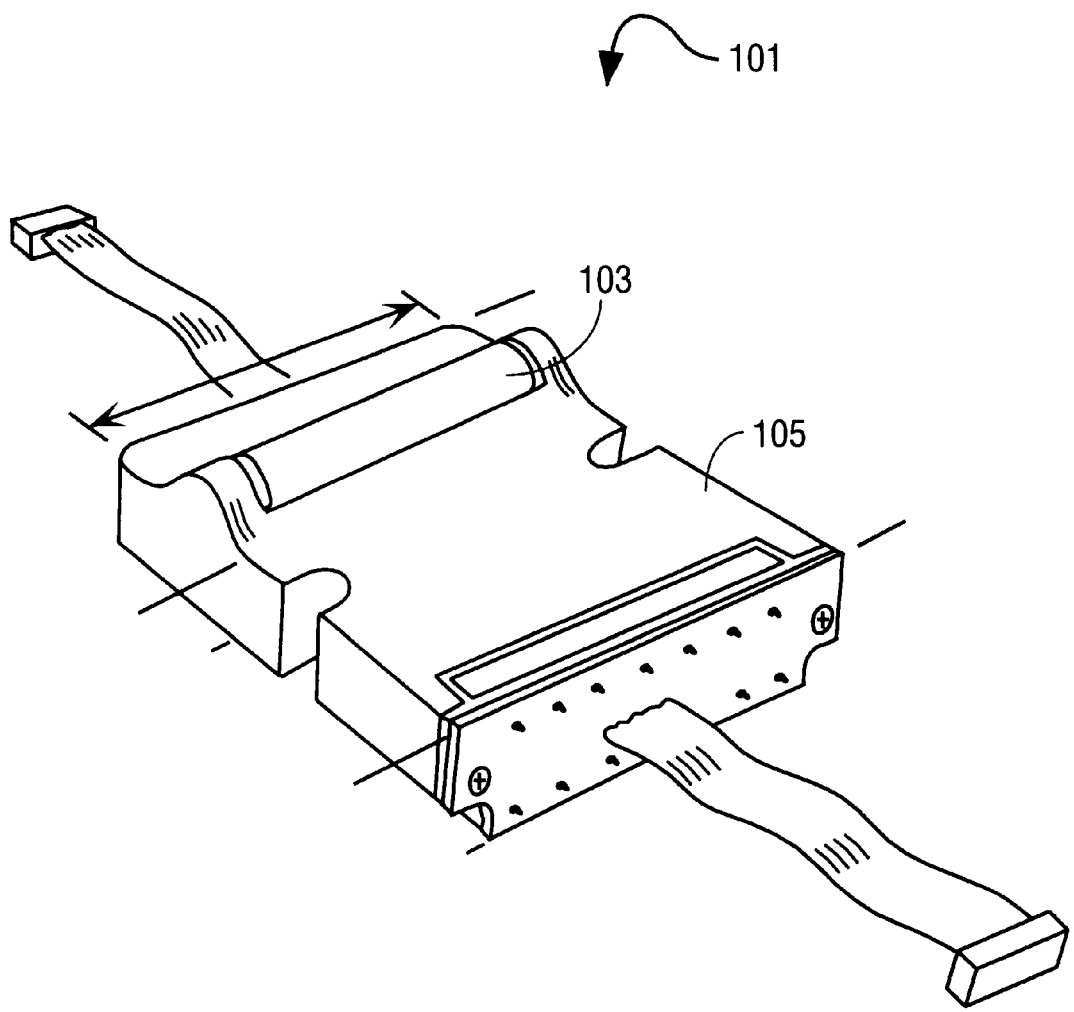
FIG. 1 is a perspective view of one embodiment of a fingerprint scanning system compatible with the present invention.
Figure 2:
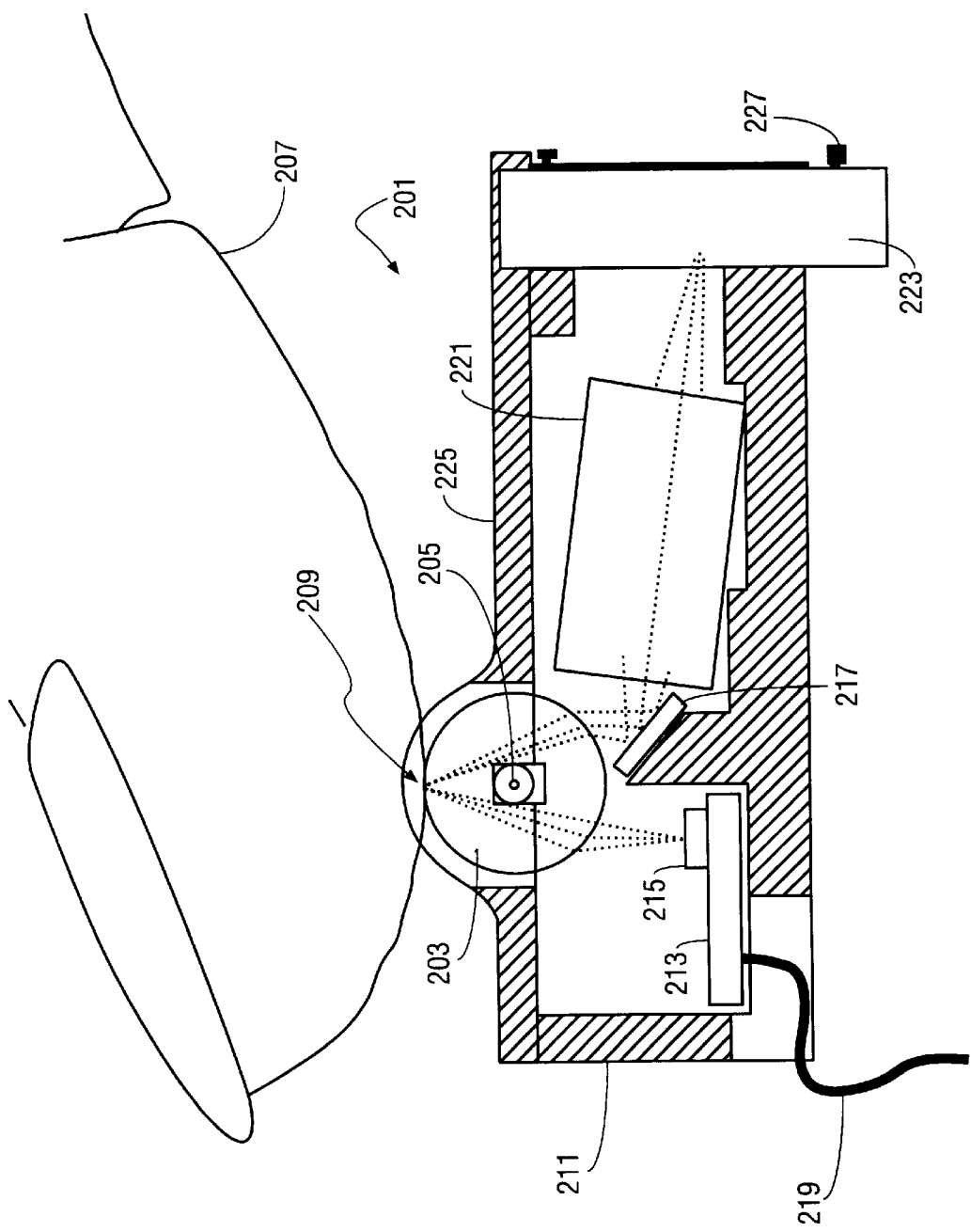
FIG. 2 is a left cut-away view of a fingerprint scanning system compatible with the present invention.

FIG. 1 shows a perspective view of an embodiment of the present invention. A fingerprint scanning apparatus 101 incorporates a transparent roller 103 and an optional finger guide 105. FIG. 2 shows a left cut-away view of an embodiment 201 of the present invention. A finger 207 or palm is rolled over a transparent roller 203 having a rotation point 205, providing a point of contact 209 with the finger 207. A light source 215, coupled to light control electronics 213 with electronic wiring 219, directs light through the roller 203 to illuminate the finger 207. Light directed through the roller 203 is focused onto a linear imaging device 223, having output wiring 227. A focusing device 221 and optional mirror 217 may be used to focus light onto the linear imaging device 223. A finger guide 225 may be optionally positioned adjacent to the roller 203 for finger alignment and to prevent distortion of the finger due to excess pressure. The scanning apparatus 201 is contained in housing 211. The light source 215 may preferably be a light emitting diode (LED), but it will be recognized by one of ordinary skill in the art that other light sources may be used with the present invention without loss of generality as long as the light source is approximately uniform across the roller 203. The focusing device 221 may preferably be a lens, but it will be recognized by one of ordinary skill in the art that other focusing devices, such as a SELFOC lens or curved mirror, may be used with the present invention without loss of generality. The linear imaging device 223 may preferably be a charge-coupled device (CCD), but it will be recognized by one of ordinary skill in the art that other imaging devices, such as a complementary metal-oxide semiconductor (CMOS) sensor or a contact image sensor (CIS), may be used with the present invention without loss of generality.

The present invention incorporates a rotation detector mechanism to detect rotational movement of the transparent roller. Both the speed and direction of the rotation may be detected. In one embodiment, a slotted code or encoder wheel may be attached orthogonally to the longitudinal axis of the roller, and a second light source may direct light through the slotted wheel. Movement of the slotted wheel, and thereby the roller, may be determined by a light detector positioned to detect light which has passed through wheel. In another embodiment of the present invention, roller indicia such as bumps or pits are placed on one side of the roller. Movement of the roller may be determined by mechanical or optical means which detects movement of the bumps or pits. In another embodiment of the present invention, roller indicia such as optical markings or decals are placed on one side of the roller. The movement of the markings or decals, and thereby the roller, may be determined by the linear imaging device used to capture an image of the fingerprint, or by separate optical detection means. It will be recognized by one of ordinary skill in the art that other mechanisms for detecting rotational movement of the roller may be used with the present invention without loss of generality.

Figure 3:
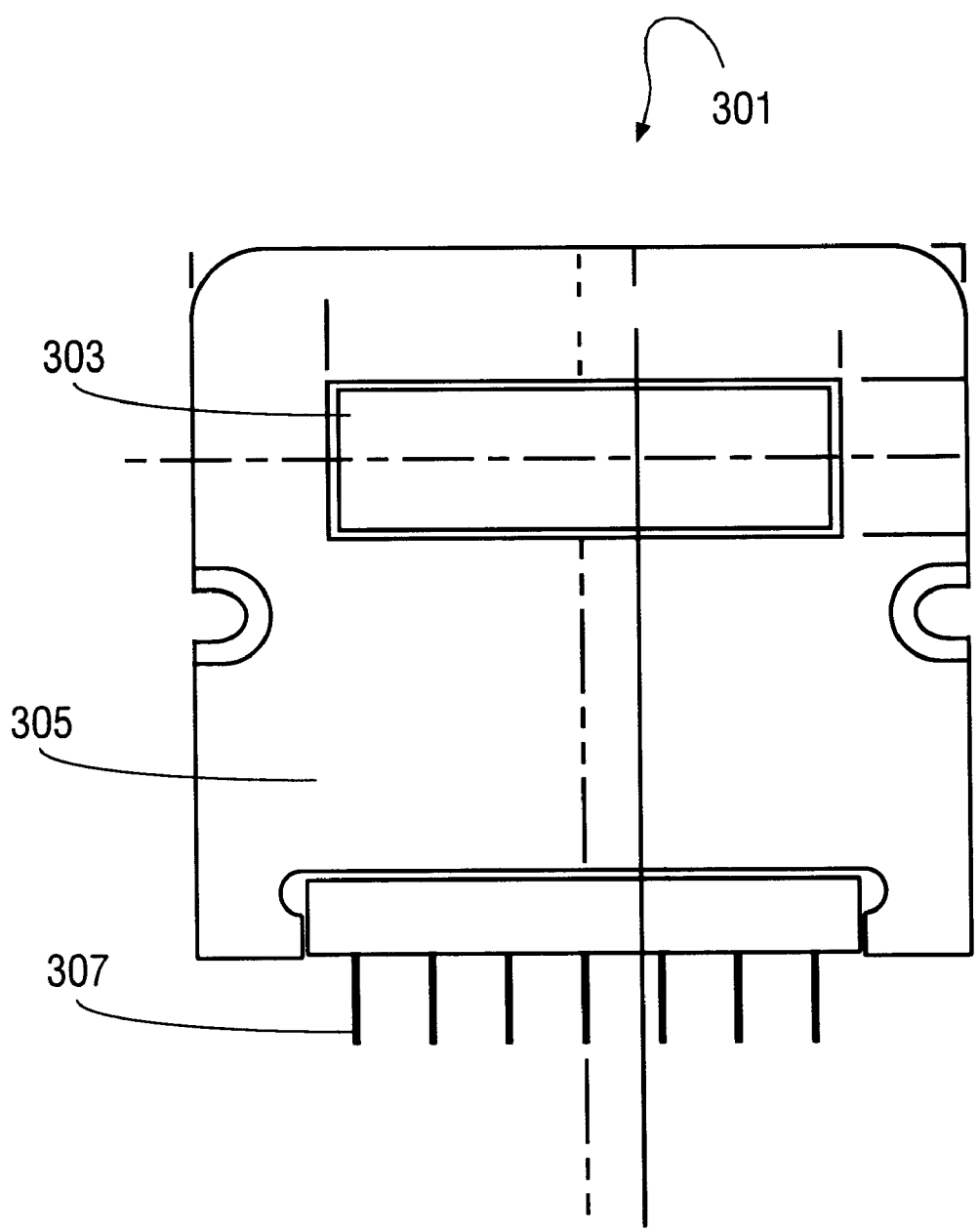
FIG. 3 is a top view of a fingerprint scanning system compatible with the present invention.

FIG. 3 shows a top view of an embodiment of the present invention. A fingerprint scanning apparatus 301 incorporates a transparent roller 303 and an optional finger guide 305. Output wiring 307 is used to output the results of the scan.

Figure 4:
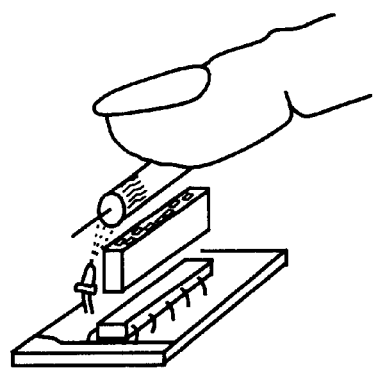
FIG. 4 is a perspective view of a vertical fingerprint scanning system compatible with the present invention.
Figure 5:
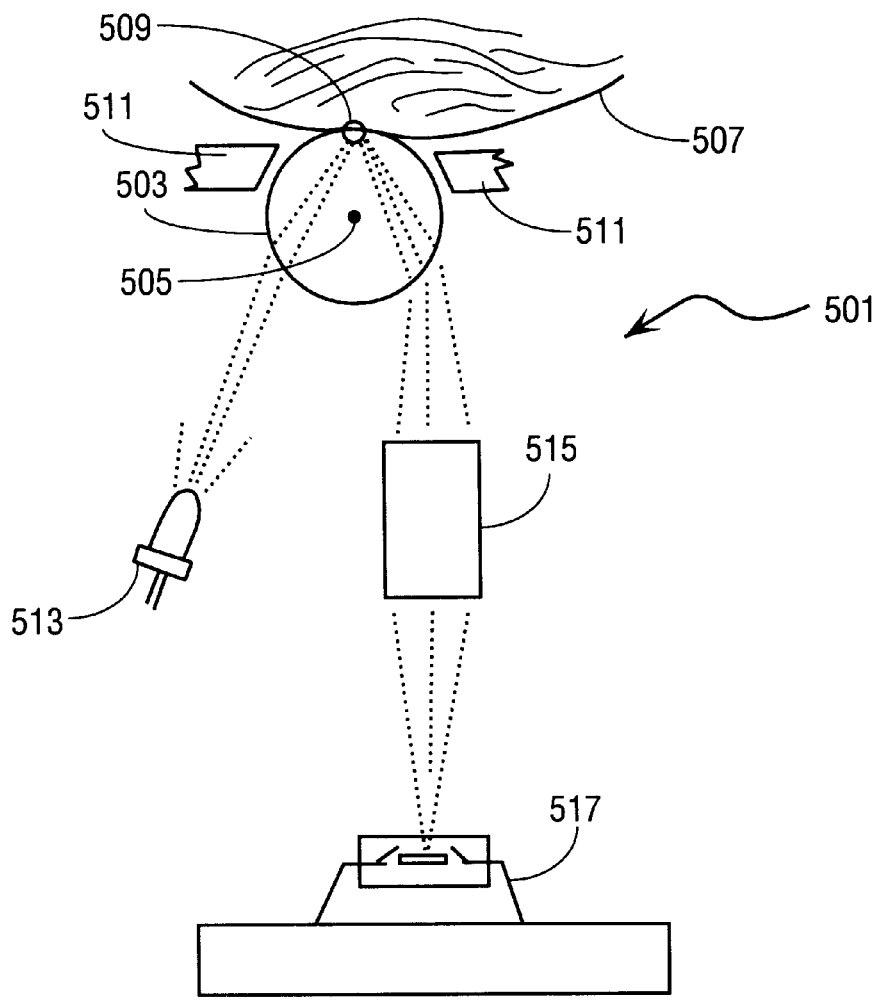
FIG. 5 is a horizontal view of one embodiment of a vertical fingerprint scanning system compatible with the present invention.

FIG. 4 and FIG. 5 show a perspective and horizontal view of a vertical embodiment 501 of the present invention. A finger 507 or palm is rolled over a transparent roller 503 having a rotation point 505, providing a point of contact 509 with the finger 507. A light source 513 directs light through the roller 503 to illuminate the finger 507. A component of the light directed through the roller 503 is focused onto a linear imaging device 517. A focusing device 515 may be used to focus light onto the linear imaging device 517. A finger guide 511 may be optionally positioned adjacent to the roller 503 to prevent distortion of the finger due to excess pressure.

Figure 6:
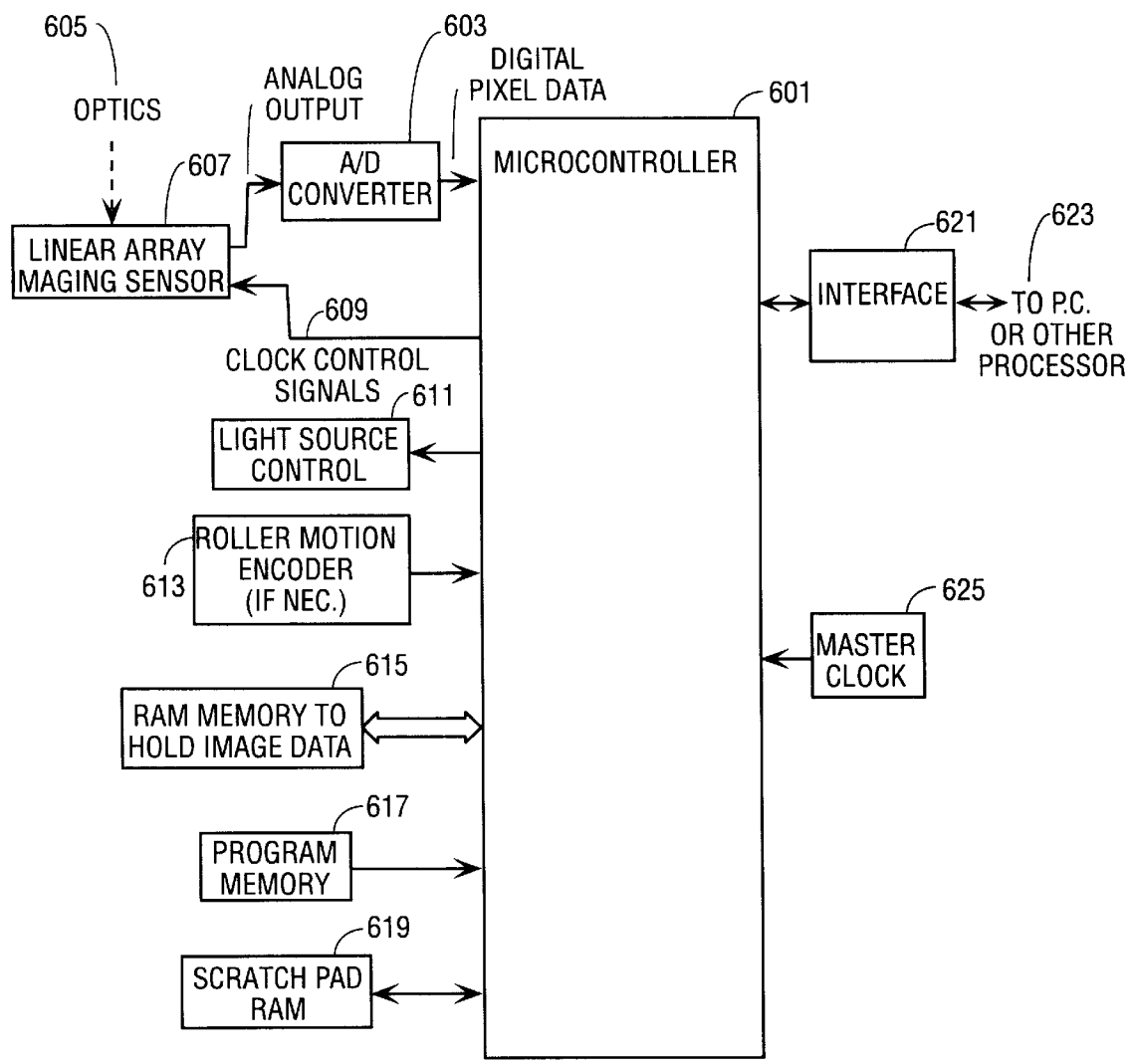
FIG. 6 is a block diagram of one embodiment of the components of a fingerprint scanning system compatible with the present invention.

FIG. 6 shows a block diagram of the components of an embodiment of the present invention. Optics 605 focuses light or image information from a finger onto a linear array imaging sensor 607, the output of which passes through an analog to digital (A/D) converter before being sent to a micro controller 601. Optional clock signals 609 from the micro controller 601 allow the image to be scanned continuously or to be captured at discrete time intervals. The micro controller 601 provides control signals to a light source control 611 to turn the light source on and off. Signals relating to the motion of the roller are sent to the micro controller 601 at 613. Memory device 615, preferably random access memory (RAM), provides an electronic storage area for the fingerprint image. A program memory 617 holds software instructions for the micro controller 601, and a temporary memory 619 holds intermediate and temporary information. An electronic interface 621 transfers information to and from an external device 623. A master clock 625 provides timing information to the micro controller 601. A full 2D recreation of the fingerprint is assembled from the discrete line-image data collected by the linear array imaging sensor 607.

Figure 7:
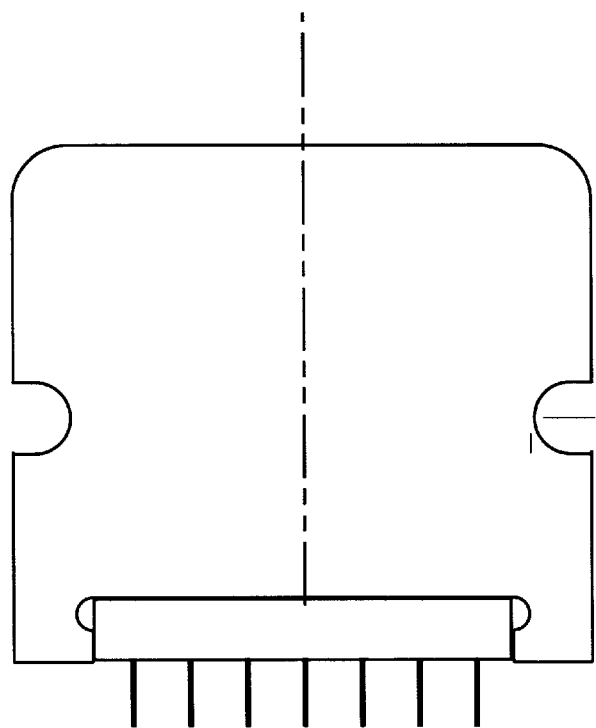
FIG. 7 is a bottom view of a fingerprint scanning system compatible with the present invention.
Figure 8:
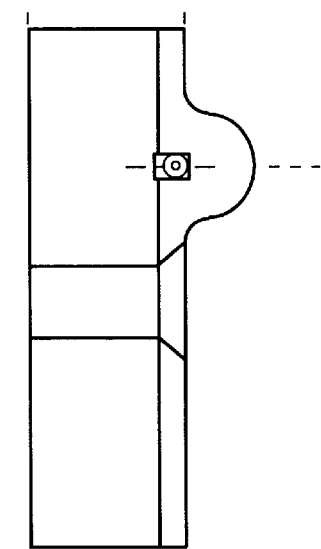
FIG. 8 is a left external view of a fingerprint scanning system compatible with the present invention.

FIG. 7 shows a bottom view of an embodiment of the present invention. FIG. 8 shows a left external view of an embodiment of the present invention.

Figure 9:
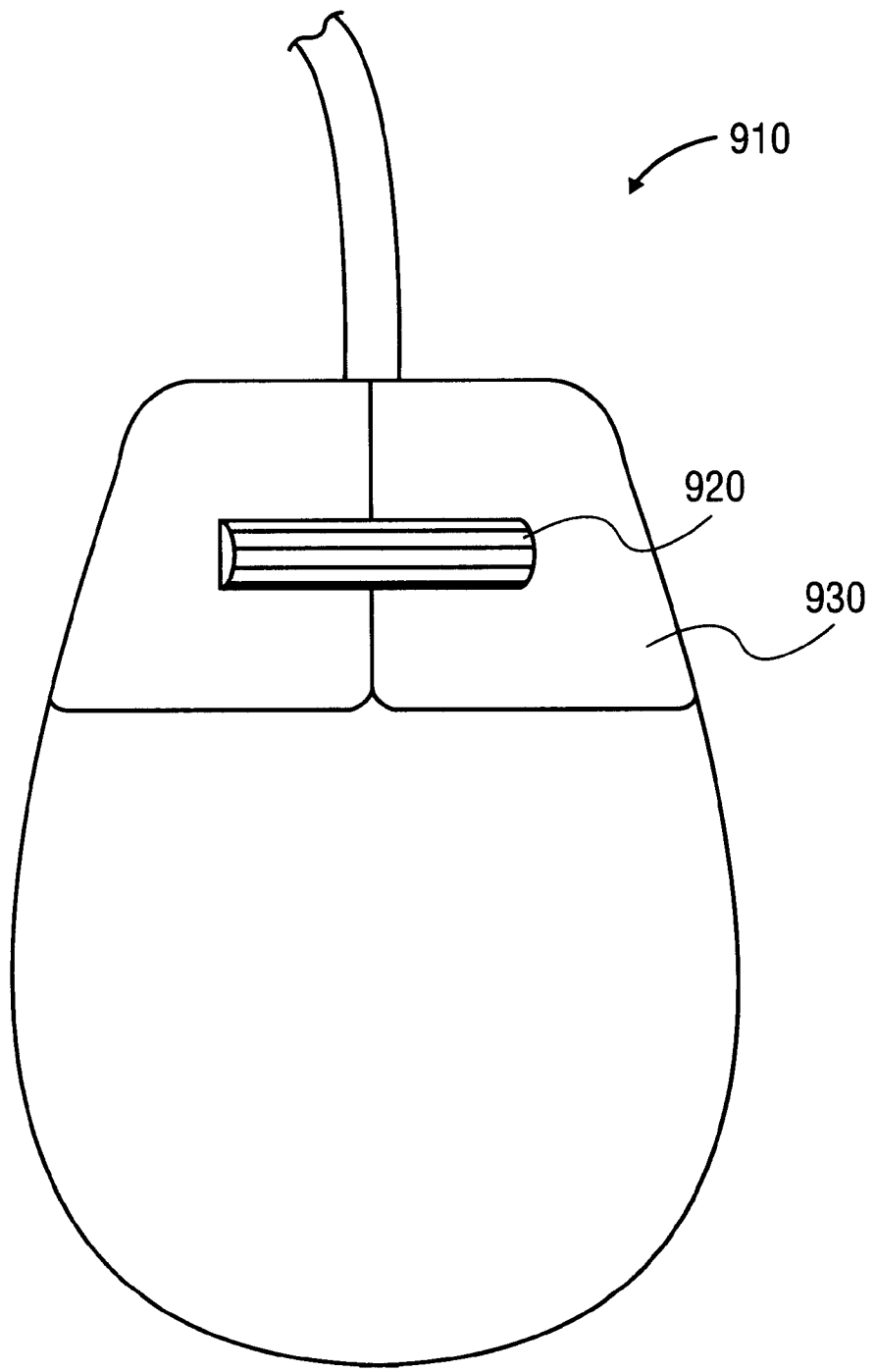
FIG. 9 is a top view of one embodiment of a mouse including one embodiment of a fingerprint scanning system.

FIG. 9 is a top view of a mouse including the fingerprint scanning system compatible with the present invention. The mouse 910 includes a scroll bar 920. The scroll bar 920 may be used to move a cursor within a window. The scroll bar 920 is further a transparent roller, as described above, to acquire a fingerprint of the user. The scroll bar 920 may light up when the cursor is positioned over an area requesting a fingerprint, or other type of authorization. In this way, the scroll bar 920 may indicate to the user that the user should use the scroll bar to enter a fingerprint into the system. The mouse 910 may further include one or more buttons. For one embodiment, the scroll bar 920 may be used as a scrolling wheel, to move a page without affecting the cursor location. This technology is known in the art. Such a scrolling and zooming wheel lets users enjoy universal scrolling in applications directly from their mouse without having to use the scrollbars.

Figure 10:
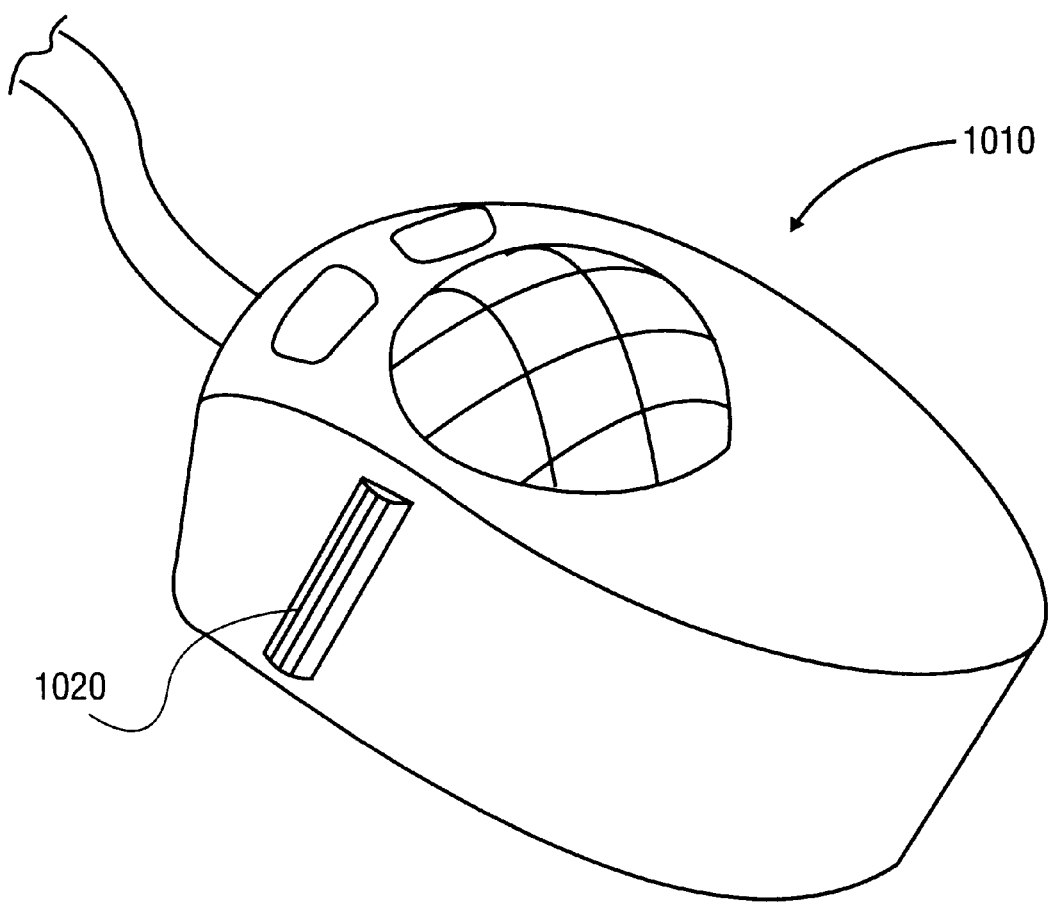
FIG. 10 is a top view of one embodiment of a trackball including one embodiment of a fingerprint scanning system.

FIG. 10 is an alternative embodiment of a mouse or track ball including the fingerprint scanning system compatible with the present invention. The track ball 1010 includes a side scroll bar 1020, with which the user may move the cursor on the screen, and which the user may use to enter a fingerprint into the system. For one embodiment, the side scroll bar 1020 may further be used as a button, by permitting clicking of the transparent roller forming the side scroll bar 1020.

Figure 11:
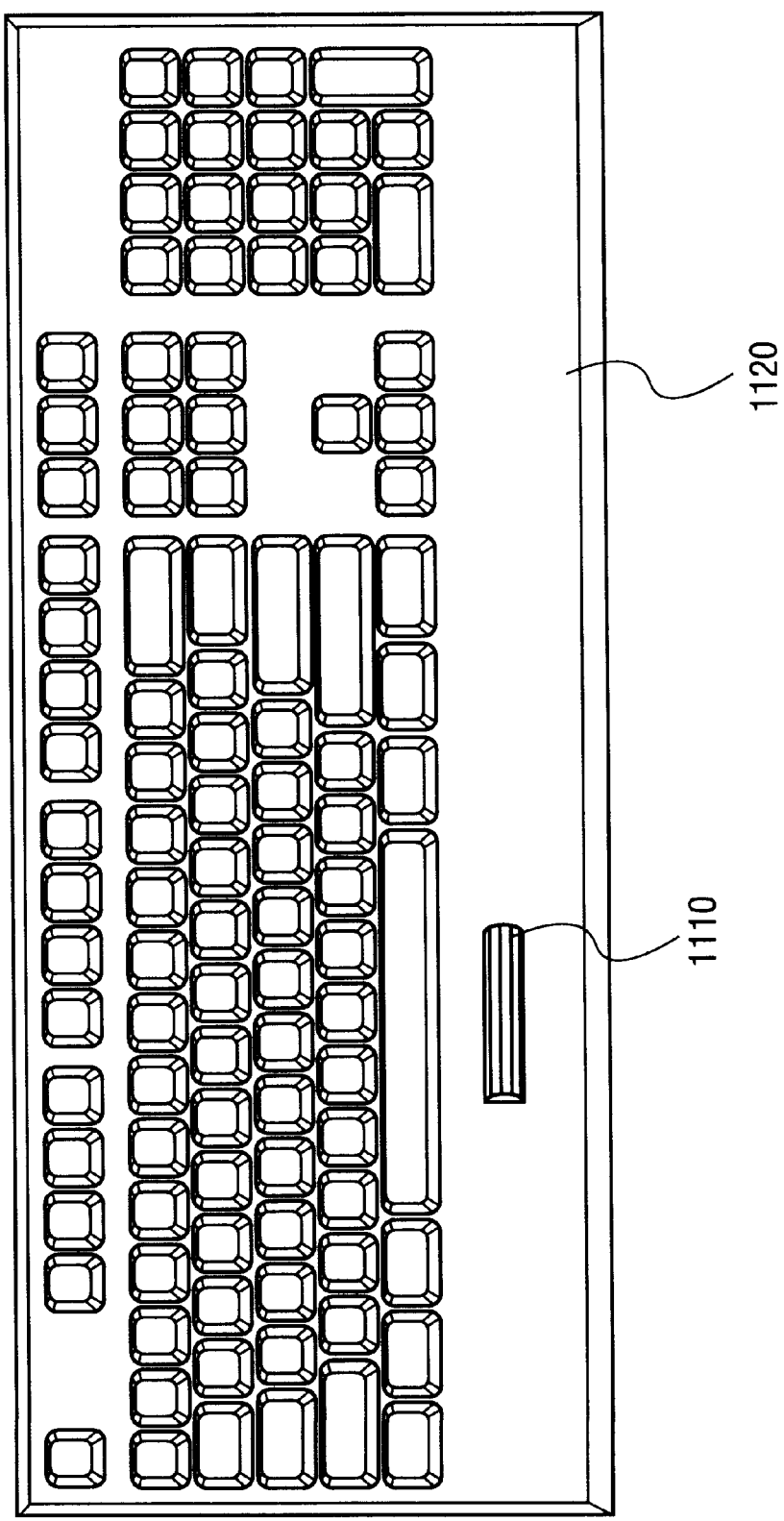
FIG. 11 is a view of an alternative embodiment of a cursor control device including one embodiment of a fingerprint scanning system.

FIG. 11 is yet another alternative embodiment of a cursor control device 1110 that incorporates the fingerprint scanning system of the present invention. The cursor control device 1110 is shown in a keyboard 1120. The cursor control device 1110 behaves as a mouse, controlling the movement of the cursor on the screen. For one embodiment, the cursor control device 1110 is similar to a pointer stick, where minor finger movements define a direction and speed of motion of the cursor. For one embodiment, the detection of cursor movement may be done by the imaging device. In other words, the movement of the user's finger along the cursor control device 1110 is detected by the imaging device. The cursor control device 1110 also forms the transparent roller of the fingerprint scanning device.

For one embodiment, when a cursor is located over an authentication area, i.e. an area requesting a fingerprint or other authentication, the cursor control device 1110 lights up, indicating to the user that the user should enter his or her fingerprint. For one embodiment, if the user does not wish to use the fingerprint scanning device, the user may abort this function in various ways.

It is to be understood that three specific implementations of the fingerprint scanning device in a cursor control device are discussed above with respect to FIGS. 9, 10, and 11. However, one skilled in the art would understand how to extend this description to other embodiments, implementing other types of cursor control mechanisms.

Figure 12:
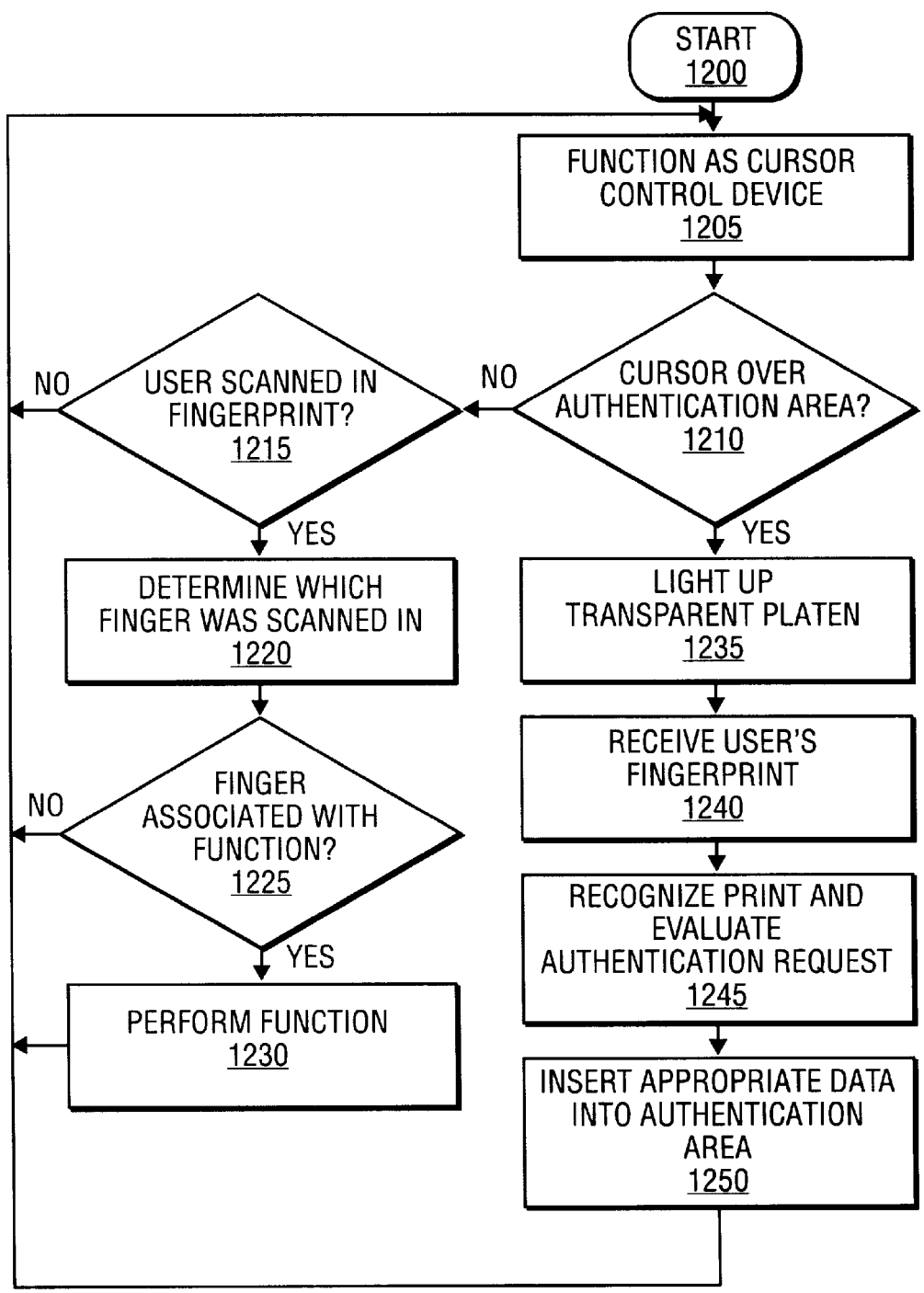
FIG. 12 is a flowchart of one embodiment of recognizing an authentication area and inserting the fingerprint.

FIG. 12 is a flowchart of recognizing an authentication area and inserting the fingerprint. The process starts at block 1200, when the fingerprint scanning device is coupled to the computer system. For one embodiment, the fingerprint scanning device may be set up as a dongle, such that the fingerprint scanning device must be coupled to the computer system, otherwise the computer system does not start up. In such a situation, the computer system may automatically request a fingerprint from a user, prior to permitting the user access to the computer system. The fingerprint scanning device may be any of the devices described above, or another type of device.

At block 1205, the fingerprint scanning device functions as a standard scroll bar or cursor control device.

At block 1210, the process determines whether the cursor is located over an authentication area. An authentication area may be any area in a screen that requests a fingerprint, a password, or other authentication data. The software recognizes a dialog box requesting authentication data.

If the cursor is not located over an authentication area, the process continues to block 1215. At block 1215, the process determines whether a user has scanned his or her fingerprint into the system. For one embodiment, the user may scan his or her fingerprint without prompting. For one embodiment, this may be detected by monitoring the input data from the fingerprint scanning device, and determining whether an entire fingerprint has been scanned. If the entire fingerprint has been scanned, the process continues to block 1220. Otherwise, the process returns to block 1205.

At block 1220, the process determines which finger of the user was scanned. For one embodiment, the user may have multiple fingers registered with the system. The registration of fingers, and the recognition of fingerprint patterns is known in the art, and may be performed by any means.

At block 1225, the process determines if there is a function associated with the user's finger. The user may associate various functions with each finger. For example, the user may scan his or her ring finger, to automatically start up a certain web page in a secure mode. Alternative functions, such as starting applications, logging into a site, or otherwise performing a series of steps may also be registered for a finger. If there is a function associated with the user's finger, that function is performed at block 1230. If no function is associated with the user's finger, the process returns to block 1205. For one embodiment, the process may further indicate to the user that no functions associated with the scanned finger were found. In this way, the user can cause the system to trigger a function based on entering a fingerprint.

If, at block 1210, the cursor was over an authentication area, the process continued to block 1235. At block 1235, the transparent roller is lit up. This indicates to the user that a fingerprint is requested.

At block 1240, the fingerprint is received from the user. For one embodiment, if the user does not enter his or her fingerprint, the system may prompt the user to enter a fingerprint. For another embodiment, if no fingerprint is received, no prompt is sent, and it is assumed that the user did not wish to enter his or her fingerprint. For yet another embodiment, the user may abort the fingerprint request by pressing a key, a mouse control button, or by other means.

At block 1245, the user's fingerprint is recognized, and the authentication requested is evaluated. The authentication may request a fingerprint directly. In that instance, the fingerprint data is inserted into the dialog box. For one embodiment, the fingerprint data may be the digital fingerprint image. For another embodiment, the fingerprint data may be a list of minutiae extracted from the fingerprint by the computer system. For another embodiment, the fingerprint may be an encrypted data derived from the fingerprint. The authentication request may request other data, such as a password. For one embodiment, the user may associate passwords and other authentication data with his or her fingerprint.

At block 1250, the appropriate data is inserted into the authentication request. As described above, this may be anything from a fingerprint image to a password. The process then returns to block 1205.

Figure 13:
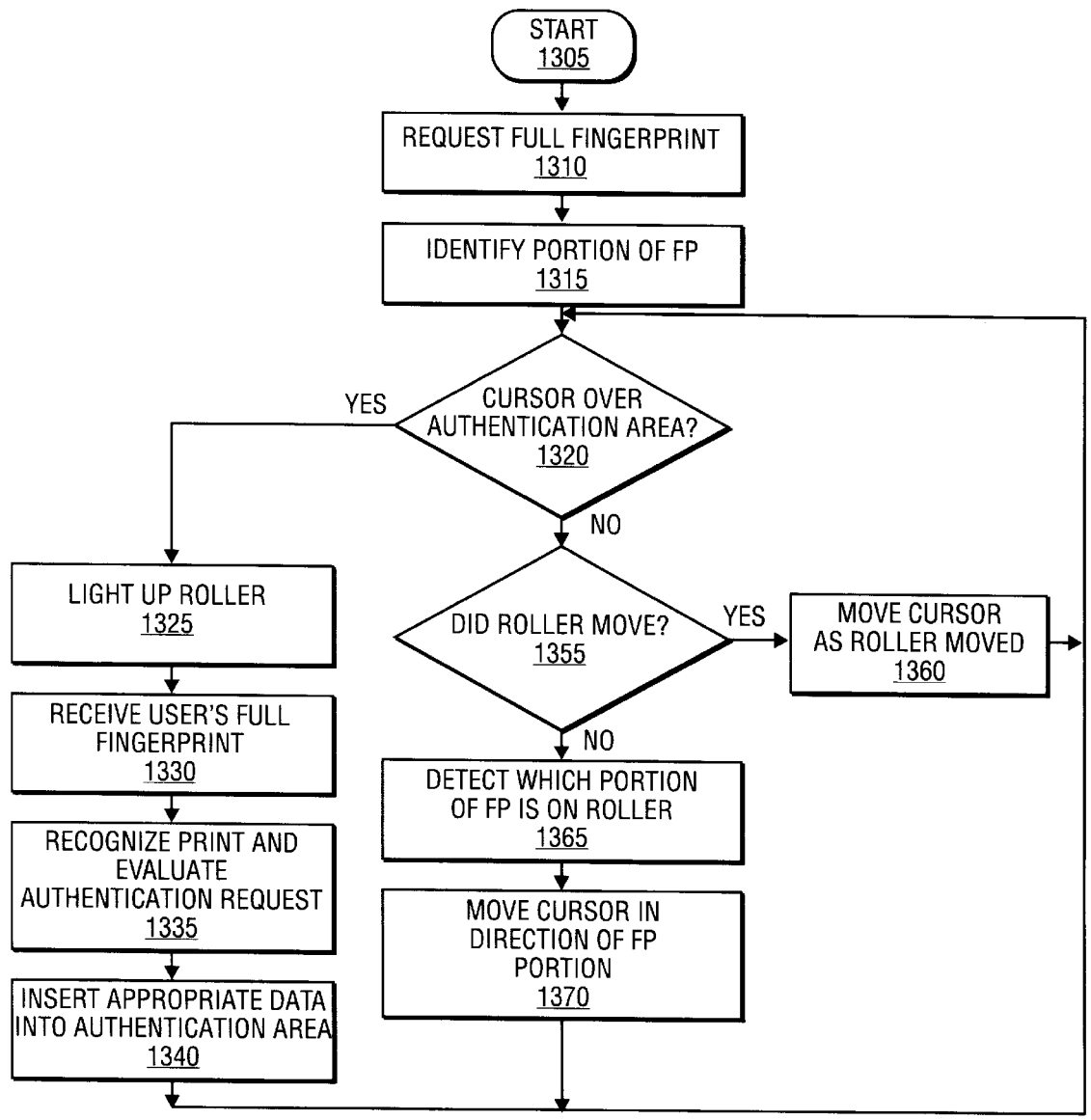
FIG. 13 is a flowchart of one embodiment of using the system as a cursor control and authentication device.

FIG. 13 is a flowchart of one embodiment of using the system as a cursor control and authentication device. The process starts at block 1305, when the system is initially turned on. A full fingerprint is requested, at block 1310. This fingerprint is processed, and the portions of the fingerprint are identified, at block 1315. The portions of the fingerprint are used to identify which part of a user's finger is on the roller at any time.

At block 1320, the process determines whether the cursor is over an authentication area. An authentication area is one that requests either a password or fingerprint, or other authentication information.

If the cursor is over an authentication area, the process continues to block 1325. At block 1325, the fingerprint sensor is lit up. For one embodiment, an LED or similar light is used. For one embodiment, this may be the light that is used to capture the fingerprint. Such a light indicates to the user that a full fingerprint is requested.

At block 1330, the user's full fingerprint is received. For one embodiment, if within a period of time, such as ten seconds, the user's fingerprint is not received, the user is alerted using a dialog box or similar mechanism.

At block 1335, the fingerprint is identified, as is known in the art, and the authentication request is evaluated. The authentication request may be asking for a particular password, for fingerprint data, or for other data. The process determines what the authentication request is for, e.g. what it is requesting. For one embodiment, the context of the URL, and other data may be used to evaluate the authentication request.

At block 1340, the appropriate data is inserted into the authentication request. This completes the authentication request. For one embodiment, if the authentication request is for data that is not available in a database of authentication, the user may be prompted to enter authentication data. For another embodiment, the user may authorize the present system to generate a random authentication data, and associate it with the current location and authentication request. This permits more complex and harder to hack passwords or authentication mechanisms. The process then returns to block 1320.

If the cursor was not found to be over an authentication area at block 1320, the process continues to block 1355.

At block 1355, the process detects whether the roller moved. If the roller moved, this indicates that the cursor should move in the appropriate direction. At block 1360, the cursor is moved in the direction in which the roller moved. For one embodiment, this defines the movement of the cursor along the Y axis. The process then returns to block 1320.

If the roller did not move, at block 1355, the process detects which portion of the fingerprint is on the roller, at block 1365. For one embodiment, this is done by comparing the portion of the fingerprint that is detected on the roller with the known fingerprint, and determining which portion of the fingerprint is on the roller.

At block 1370, the cursor is moved in the direction which corresponds to the fingerprint portion on the roller. For one embodiment, the system temporarily stores the fingerprint area detected, and does a preliminary comparison with the stored area, to reduce the detection time/computational intensity. If the fingerprint portion does not correspond to a resting fingerprint (e.g. to the center of the finger area) the cursor is moved as appropriate. This defines the movement of the cursor along the X axis. For one embodiment, the two detections, cursor movement and fingerprint area may be done simultaneously. The process then returns to block 1320. For one embodiment, for a roller which is being used as a scroll wheel, rather than a full control device, blocks 1365 and 1370 may be eliminated. In that instance, at block 1360, the display is moved in response to a movement of the roller, and the cursor itself is not affected.

Note that although this process was described as a sequence of events in a flowchart, the actual implementation may run separate loops for detecting the authentication area, and the movement of the cursor along the X-axis and the Y-axis.

Figure 14:
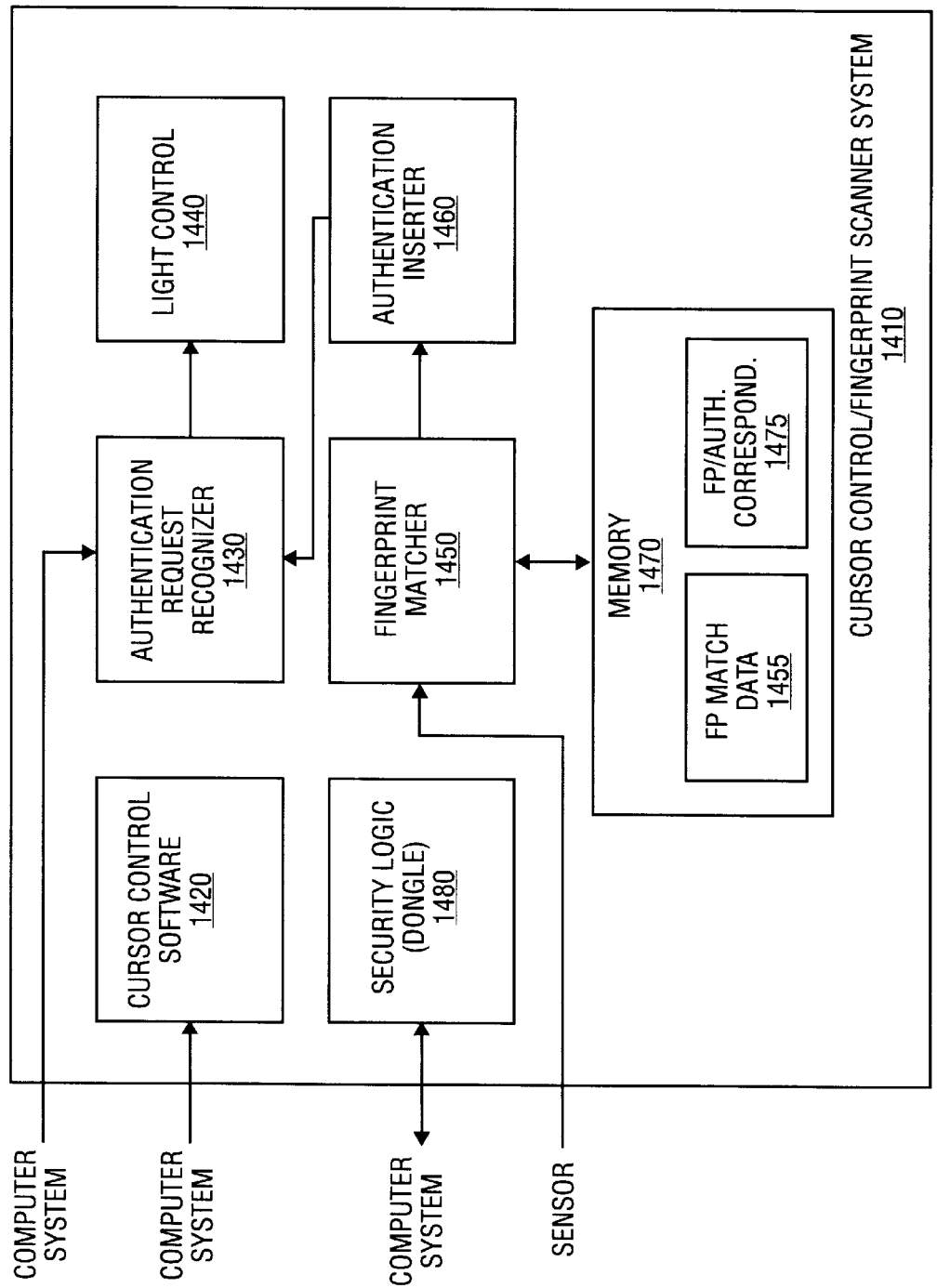
FIG. 14 is a block diagram of one embodiment of the software application for the system.

FIG. 14 illustrates a block diagram of one embodiment of the software application for the system. The cursor control/ fingerprint scanner (CCFS) system 1410 includes cursor control software 1420. For one embodiment, the cursor control software 1420 may include a scroll bar software and/or cursor control software. For another embodiment, if the system scanning apparatus is used for fingerprint sensing and cursor control the cursor control software 1420 may be as described above with respect to FIG. 13. For one embodiment, the process described may parallel that of patent application Ser. No. 09/153,782. For one embodiment, the cursor control software 1420 may be located outside the CCFS system 1410.

The CCFS system 1410 further includes an authentication request recognizer 1430. The authentication request recognizer recognizes a dialog box or other area displayed on the computer system that requests authentication information. As discussed above, this may be implemented in various ways. For one embodiment, the authentication request recognizer 1430 may monitor the software drawing dialog boxes, and determine when a dialog box requesting authentication information is drawn. Systems for recognizing when authentication data is requested are known in the art.

The CCFS system 1410 further includes a light control 1440. The light control 1440 receives data that the cursor is over an authentication area from the authentication request recognizer 1430, and lights up the transparent roller area, to prompt the user to enter his or her fingerprint into the system.

The fingerprint matcher 1450 receives the fingerprint from the sensor (not shown) and determines whether the fingerprint is the print of the user. For one embodiment, the fingerprint matcher 1450 may further recognize multiple prints of a single user, if multiple prints are registered. For one embodiment, the fingerprint matcher 1450 uses fingerprint match information 1455 in the memory 1470, to determine whether the print is of the user, and which print of the user's has been entered.

The authentication inserter 1460 determines the type of data requested by the authentication area, and determines whether the user has a matching authentication data in the correspondence area 1475 of memory 1470. If matching authentication data is found in memory 1470, the authentication inserter 1460 inserts the authentication data into the authentication area. For one embodiment, the correspondence area 1475 is a database of various passwords and authentication functions as registered by the user. Registering such passwords and authentication functions are known in the art.

For one embodiment, the CCFS system 1410 further includes security logic 1480. The security logic 1480 permits the fingerprint scanner to act as a dongle, not permitting access to a computer system or other device to which the fingerprint scanner may be coupled, unless an authorized fingerprint is received. For one embodiment, the security logic 1480 interfaces with the computer system, to provide an authorization code to access the system. This type of logic is known in the art.

For one embodiment, the CCFS system 1410 may be located on the main system, such as a computer system. For another embodiment, the CCFS system 1410 may be located on the cursor control device. For yet another embodiment, the CCFS system 1410 may be distributed between the main system and the cursor control device, such that secure information, such as the memory 1470 and the security logic 1480 may be located on the cursor control device, while other computing intensive portions of the CCFS 1410 are implemented on the main system.

Although the term computer system was used in describing the functionality of FIG. 14, it is to be understood that any system that can perform computing functions may be considered a computer system for the present invention.

For another embodiment, the cursor control functionality may be independently implemented. In that case, the system need not include the cursor control software portion of the system.

While the invention is described in terms of preferred embodiments in a specific system environment, those of ordinary skill in the art will recognize that the invention can be practiced, with modification, in other and different hardware and software environments within the spirit and scope of the appended claims.

What is claimed is:

1. An apparatus for a cursor control device that may be used for scanning a fingerprint comprising:

a roller for controlling a display; and a fingerprint scanning device comprising:
- a linear imaging device;
- a light source positioned to direct light through the roller;
- a focusing device positioned to focus light directed through the roller onto the linear imaging device;

such that the roller is used to control a cursor and for fingerprint scanning.

2. The apparatus of claim 1, further comprising a rotation detector to detect rotational movement of the roller.

3. The apparatus of claim 2, wherein the rotation detector comprises:
- a slotted wheel coupled to the roller;
- a second light source positioned to direct light through the slotted wheel; and
- a light detector positioned to detect light directed through the slotted wheel.

4. The apparatus of claim 2, wherein the rotation detector comprises:
- roller indicia; and
- an indicia detector positioned to detect movement of the indicia.

5. The apparatus of claim 4, wherein the indicia detector comprises the linear imaging device.

6. The apparatus of claim 4, wherein the roller indicia comprises markings selected from the group consisting of bumps, pits, ridges, slots, optical decals, and optical marks.

7. The apparatus of claim 1, further comprising a finger guide positioned adjacent to the roller.

8. The apparatus of claim 1, wherein controlling the cursor comprises using the roller as a scrolling and zooming wheel that provides universal scrolling in applications directly from the cursor control device without using scrollbars.

9. The apparatus of claim 1, wherein the roller controls cursor movement directly.

10. The apparatus of claim 9, wherein the linear image device recognizes a movement of the finger on the roller, and further comprising a cursor control software for determining an appropriate movement of the cursor based on the movement of the finger on the roller.

11. The apparatus of claim 1, wherein the apparatus is embedded in one of the following devices: a mouse, a trackball, or a keyboard.

12. The apparatus of claim 1, further comprising software for recognizing an area requesting authentication information and prompting a user for the fingerprint.

13. The apparatus of claim 12, wherein the software further comprises:

light control for lighting up the roller when the cursor is over the area requesting authentication information.

14. The apparatus of claim 12, wherein the software further comprises:

an authentication inserter for inserting authentication information into the area requesting authentication information based on the user's fingerprint.

15. A method for using a cursor control device for scanning a fingerprint comprising:

controlling a cursor in response to movement of a roller;

determining if the cursor is over an authentication area; and if the cursor is over an authentication area:
- lighting up the roller; and
- illuminating a finger with light directed through the roller; and
- capturing an image of the fingerprint through the roller with a linear imaging device.

16. The method of claim 15, further comprising:

recognizing the fingerprint; and inserting an appropriate authentication information in the authentication area, based on the fingerprint.

17. The method of claim 16, wherein inserting comprises:

determining whether the authentication area requests fingerprint data or other data; and inserting fingerprint data into the authentication area if the authentication area requests fingerprint data; and looking up other data in a memory if the authentication area requests other data, and inserting other data into the authentication area.

18. The method of claim 15, further comprising:

recognizing a fingerprint received from the linear imaging device;

determining whether the fingerprint is associated with a function; and if the fingerprint is associated with a function, performing the function.

19. The method of claim 15, wherein controlling the cursor comprises moving the cursor in response to a user's finger movement on the roller.

20. The method of claim 15, wherein controlling the cursor comprises scrolling the display or zooming the display in response to a user using the roller.

* * * * *